United States Patent [19]

Rainer

[11] 4,381,301
[45] Apr. 26, 1983

[54] SUBSTITUTED TRICYCLIC THIENO COMPOUNDS, THEIR SYNTHESIS, THEIR USE, THEIR COMPOSITIONS AND THEIR MEDICAMENTS

[75] Inventor: Georg Rainer, Constance, Fed. Rep. of Germany

[73] Assignee: BYK Gulden Lomberg Chemische Fabrik GmbH, Fed. Rep. of Germany

[21] Appl. No.: 175,244

[22] Filed: Aug. 4, 1980

[30] Foreign Application Priority Data

May 7, 1980 [CH] Switzerland .................. 3581/80

[51] Int. Cl.$^3$ .................. A61K 31/495; C07D 521/00
[52] U.S. Cl. .................. 424/250; 424/248.51; 424/267; 424/274; 424/275; 260/239.3 T
[58] Field of Search .............. 260/243.3, 244.4, 330.3, 260/245.7, 239.3 T; 424/250, 248.51, 267, 274, 424/275

[56] References Cited

U.S. PATENT DOCUMENTS

| | | | |
|---|---|---|---|
| 3,660,380 | 5/1972 | Schmidt | 260/239.3 |
| 3,743,734 | 7/1973 | Schmidt | 424/250 |
| 3,951,981 | 4/1976 | Safir | 260/243.3 |
| 3,953,430 | 4/1976 | Safir | 260/239.3 T |
| 4,021,557 | 5/1977 | Schmidt et al. | 260/244.4 |
| 4,087,421 | 5/1978 | Safir | 260/243.3 |
| 4,115,574 | 9/1978 | Chakrabarti et al. | 260/244.4 |
| 4,144,235 | 3/1979 | Press et al. | 260/239.3 T |
| 4,168,269 | 9/1979 | Brabander | 260/330.3 |
| 4,172,831 | 10/1979 | Chakrabarti et al. | 260/239.3 T |
| 4,263,207 | 4/1981 | Rokach et al. | 260/239.3 T |

FOREIGN PATENT DOCUMENTS 1505795 12/1967 France.

OTHER PUBLICATIONS

Rote Liste 1981, 59 344 and 59 354, Editio Cantor.
Carter, et al., *Chemotheraph of Cancer*, 2nd Ed., John Wiley & Sons, N.Y., 1981, pp. 168–173.

*Primary Examiner*—Donald G. Daus
*Assistant Examiner*—James H. Turnipseed
*Attorney, Agent, or Firm*—Berman, Aisenberg & Platt

[57] ABSTRACT

Substituted thienobenzodiazepinones of the general formula I

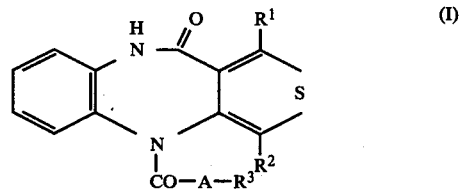

[wherein $R^1$ denotes a hydrogen atom (—H) or an alkyl radical with 1 to 4 carbon atoms; $R^2$ represents a halogen atom (halo) or has one of the meanings of $R^1$; $R^3$ denotes a halogen atom (halo) or the group —N($R^4$)$R^5$; $R^4$ denotes an alkyl radical with 1 to 4 carbon atoms or an alkenyl radical with 3 to 5 carbon atoms; $R^5$ has one of the meanings of $R^4$ or represents the group —(CH$_2$)$_m$—N($R^6$)$R^7$; or $R^4$ and $R^5$, together with the nitrogen atom to which both are bonded, denote a morpholino group, a pyrrolidino group, a piperidino group, a hexahydroazepin-1-yl group, a piperazin-1-yl group (which is optionally substituted in the 4-position by a methyl, ethyl or benzyl group), a 2,4-dimethylpiperazin-1-yl group, or a hexahydro-1H-1,4-diazepin-1-yl group (which is substituted in the 4-position by a methyl or ethyl group); $R^6$ denotes an alkyl group with 1 to 4 carbon atoms; $R^7$ denotes an alkyl group with 1 to 4 carbon atoms; A denotes a straight-chain or branched alkylene group with 1 to 5 carbon atoms; and m denotes 2 or 3] and their acid-addition salts are new compounds. They either have a protective action on the stomach and intestine and are suitable for treating illnesses based on disorders of the stomach or intestine, or they are intermediates for preparing products having protective action. Processes for the preparation of the new pharmacologically-active compounds and of the intermediate products are presented.

14 Claims, No Drawings

SUBSTITUTED TRICYCLIC THIENO COMPOUNDS, THEIR SYNTHESIS, THEIR USE, THEIR COMPOSITIONS AND THEIR MEDICAMENTS

TECHNICAL FIELD

The invention relates to substituted tricyclic thieno compounds, their synthesis, their use, their compositions and their medicaments.

The compounds according to the invention are used directly in the pharmaceutical industry, as intermediate products and in the preparation of medicaments.

BACKGROUND

Pyridobenzodiazepines (which are stated to have ulcus inhibitory, secretion inhibitory, antitussive and, in part, antiemetic action) and their compositions are considered in U.S. Pat. No. 3,660,380 and No. 3,743,734, respectively, whereas substituted benzodiazepinones with antidepressant and analgesic actions are referred to in U.S. Pat. No. 3,953,430. Substituted thienobenzodiazepines with analgesic action are mentioned in U.S. Pat. No. 4,168,269. Thienobenzodiazepinones which have new interesting pharmacological actions have now been found.

SUMMARY OF THE INVENTION

The encompassed compounds are thienobenzodiazepinones of the following types:
(1) 9,10-dihydro-3-halo-4-[halo(lower alkyl)carbonyl]-4H-thieno[3,4-b][1,5]benzodiazepin-10-one,
(2) 9,10-dihydro-4-[halo(lower alkyl)carbonyl]-4H-thieno[3,4-b][1,5]benzodiazepin-10-one,
(3) 9,10-dihydro-4-[halo(lower alkyl)carbonyl]-3-(lower alkyl)-4H-thieno[3,4-b][1,5]benzodiazepin-10-one,
(4) 9,10-dihydro-3-halo-4-[halo(lower alkyl)carbonyl]-1-(lower alkyl)-4H-thieno[3,4-b][1,5]benzodiazepin-10-one,
(5) 9,10-dihydro-4-[halo(lower alkyl)carbonyl]-1-(lower alkyl)-4H-thieno[3,4-b][1,5]benzodiazepin-10-one,
(6) 9,10-dihydro-1,3-di(lower alkyl)-4-[halo(lower alkyl)carbonyl]-4H-thieno[3,4-b][1,5]benzodiazepin-10-one,
(7) 9,10-dihydro-4-[(substituted amino)(lower alkyl)carbonyl]-4H-thieno[3,4-b][1,5]benzodiazepin-10-one,
(8) 9,10-dihydro-3-halo-4-[(substituted amino)(lower alkyl)carbonyl]-4H-thieno[3,4-b][1,5]benzodiazepin-10-one,
(9) 9,10-dihydro-3-(lower alkyl)-4-[(substituted amino)(lower alkyl)carbonyl]-4H-thieno[3,4-b][1,5]benzodiazepin-10-one,
(10) 9,10-dihydro-3-halo-1-(lower alkyl)-4-[(substituted amino)(lower alkyl)carbonyl]-4H-thieno[3,4-b][1,5]benzodiazepin-10-one,
(11) 9,10-dihydro-1-(lower alkyl)-4-[(substituted amino)(lower alkyl)carbonyl]-4H-thieno[3,4-b][1,5]benzodiazepin-10-one,
(12) 9,10-dihydro-1,3-di(lower alkyl)-4-[(substituted amino)(lower alkyl)carbonyl]-4H-thieno[3,4-b][1,5]benzodiazepin-10-one
and their acid-addition salts. The compounds are those which are physiologically active and useful for treating stomach and intestinal disorders or those which are intermediates in the synthesis of such compounds. The physiologically-active compounds are formulated into compositions which are prepared in standard dosage forms and administered to mammals afflicted with or subject to stomach and/or intestinal disorders.

DETAILS

The invention relates to substituted thienobenzodiazepinones of the formula

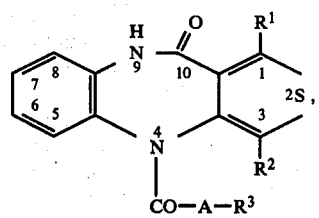

wherein
$R^1$ denotes a hydrogen atom (-H) or an alkyl radical with from 1 to 4 carbon atoms,
$R^2$ represents a halogen atom (halo) or has one of the meanings of $R^1$,
$R^3$ denotes a halogen atom (halo) or $-N(R^4)R^5$,
$R^4$ denotes an alkyl radical with from 1 to 4 carbon atoms, an alkenyl radical with from 3 to 5 carbon atoms or, together with $R^5$ and the nitrogen atom to which both are bound, a morpholino group, a pyrrolidino group, a piperidino group, a hexahydroazepin-1-yl group, a piperazin-1-yl group which is optionally substituted in the 4-position by a methyl, ethyl or benzyl group, a 2,4-dimethylpiperazin-1-yl group, or a hexahydro-1H-1,4-diazepin-1-yl group which is substituted in the 4-position by a methyl or ethyl group,
$R^5$ has one of the meanings of $R^4$, represents $-(CH_2)_m-N(R^6)R^7$ or, together with $R^4$ and the nitrogen atom to which both are bound, denotes a morpholino group, a pyrrolidino group, a piperidino group, a hexahydroazepin-1-yl group, a piperazin-1-yl group which is optionally substituted in the 4-position by a methyl, ethyl or benzyl group, a 2,4-dimethylpiperazin-1-yl group, or a hexahydro-1H-1,4-diazepin-1-yl group which is substituted in the 4-position by a methyl or ethyl group,
$R^6$ denotes an alkyl group with from 1 to 4 carbon atoms,
$R^7$ denotes an alkyl group with from 1 to 4 carbon atoms,
A denotes a straight-chain or branched alkylene group with from 1 to 5 carbon atoms and
m denotes 2 or 3,
and their acid-addition salts.

Alkyl radicals with from 1 to 4 carbon atoms are the methyl, ethyl, propyl, isopropyl, n-butyl, isobutyl, sec.-butyl and tert.-butyl radicals. Of the alkyl radicals, the methyl radical and ethyl radical are preferred in the case of $R^1$, $R^2$, $R^4$, $R^5$, $R^6$ and $R^7$. The methyl radical is particularly preferred as the alkyl radical for $R^1$ and $R^2$.

The allyl radical and the 2-methallyl radical are illustrative of alkenyl radicals with 3 to 5 carbon atoms.

Halogen atoms $R^2$ are, primarily, the bromine atom (bromo) and, in particular, the chlorine atom (chloro). Halogen atoms $R^3$ (Hal) are the iodine atom (iodo), the bromine atom (bromo) and, in particular, the chlorine atom (chloro).

Illustrative alkylene groups with from 1 to 5 carbon atoms are the trimethylene, tetramethylene, pentamethylene, 2-propylene and ethylmethylene groups, preferably the ethylene group and, in particular, the methylene group.

All the acid-addition salts are contemplated. The pharmacologically-acceptable salts of the inorganic and organic acids customarily used galenically are of particular importance. Pharmacologically-unacceptable salts are readily converted into pharmacologically-acceptable salts by conventional and well-established processes. Examples of pharmacologically-acceptable salts are water-soluble or water-insoluble acid-addition salts, such as hydrobromide, hydriodide, nitrate, acetate, benzoate, hibenzate [2-(4-hydroxybenzoyl)benzoate], fendizoate {2-[2'-hydroxy-4-biphenylyl)carbonyl]benzoate}, propionate, butyrate, sulfosalicylate, laurate, oxalate, amsonate (4,4'-diaminostilbene-2,2'-disulfonate), embonate [4,4'-methylene-bis-(3-hydroxy-2-naphthoate)], metembonate [4,4'-methylene-bis-(3-methoxy-2-naphthoate)], stearate, 2-hydroxy-3-naphthoate and 3-hydroxy-2-naphthoate and, in particular, the hydrochloride, phosphate, sulfate, citrate, gluconate, maleate, malate, fumarate, succinate, tartrate, tosylate (p-toluenesulfonate), mesylate (methanesulfonate) and amidosulfonate.

Substituted thienobenzodiazepinones I* of the formula I, wherein $R^1$ denotes a hydrogen atom (—H), or a methyl or ethyl radical, $R^2$ represents a chlorine atom (chloro) or has one of the meanings of $R^1$, $R^3$ denotes a chlorine atom (chloro) and A denotes a straight-chain or branched alkylene group with 1 or 2 carbon atoms, form an embodiment of the invention.

Preferred representatives of embodiment I* are those in which A denotes a methylene group.

A particularly preferred representative of embodiment I* is that in which each of $R^1$ and $R^2$ denotes a hydrogen atom, $R^3$ denotes a chlorine atom and A denotes a methylene group.

Substituted thienobenzodiazepinones I** of the formula I, wherein $R^1$ denotes a hydrogen atom (—H) or a methyl or ethyl radical, $R^2$ represents a chlorine atom (chloro) or has one of the meanings of $R^1$, $R^3$ denotes —N($R^4$)$R^5$, $R^4$ denotes an alkyl radical with from 1 to 4 carbon atoms, an alkenyl radical with 3 or 4 carbon atoms or, together with $R^5$ and the nitrogen atom to which both are bound, a morpholino group, a pyrrolidino group, a piperidino group, a hexahydroazepin-1-yl group, a piperazin-1-yl group which is substituted in the 4-position by a methyl, ethyl or benzyl group, a 2,4-dimethylpiperazin-1-yl group or a hexahydro-1H-1,4-diazepin-1-yl group which is substituted in the 4-position by a methyl or ethyl group, $R^5$ has the meaning of $R^4$, represents —(CH$_2$)$_m$—N($R^6$)$R^7$ or, together with $R^4$ and the nitrogen atom to which both are bound, denotes a morpholino group, a pyrrolidino group, a piperidino group, a hexahydroazepin-1-yl group, a piperazin-1-yl group which is substituted in the 4-position by a methyl, ethyl or benzyl group, a 2,4-dimethylpiperazin-1-yl group or a hexahydro-1H-1,4-diazepin-1-yl group which is substituted in the 4-position by a methyl or ethyl group, $R^6$ denotes a methyl or ethyl group, $R^7$ denotes a methyl or ethyl group, m denotes 2 or 3 and A denotes a straight-chain or branched alkylene group with 1 or 2 carbon atoms, and their acid-addition salts form a further embodiment of the invention.

A group of representatives of embodiment I** comprises those in which $R^1$ denotes a hydrogen atom (—H) or a methyl or ethyl radical; $R^2$ represents a chlorine atom (chloro) or has one of the meanings of $R^1$; $R^4$ denotes a methyl or ethyl radical or, together with $R^5$ and the nitrogen atom to which both are bound, a pyrrolidino, piperidino or hexahydroazepin-1-yl radical; $R^5$ has the meaning of $R^4$, represents —(CH$_2$)$_m$—N($R^6$)$R^7$ or, together with $R^4$ and the nitrogen atom to which both are bound, denotes a pyrrolidino, piperidino or hexahydroazepin-1-yl radical; each of $R^6$ and $R^7$ denotes a methyl or ethyl radical; m denotes 2; and A denotes a methylene group; and their pharmacologically-acceptable acid-addition salts.

Another group of representatives of embodiment I** are those in which $R^1$ denotes a hydrogen atom (—H) or a methyl or ethyl radical; $R^2$ represents a chlorine atom (chloro) or has one of the meanings of $R^1$; $R^4$ and $R^5$, together with the nitrogen atom to which both are bound, denote piperazin-1-yl (which is substituted in the 4-position by a methyl, ethyl or benzyl group), 2,4-dimethylpiperazin-1-yl or a hexahydro-1H-1,4-diazepin-1-yl group which is substituted in the 4-position by a methyl or ethyl group; and A denotes a methylene group; and their pharmacologically-acceptable acid-addition salts.

Preferred representatives of embodiment I** are those in which $R^1$ denotes a hydrogen atom (—H) or a methyl radical; $R^2$ denotes a hydrogen atom (—H) or a methyl radical; $R^4$ and $R^5$, together with the nitrogen atom to which both are bound, denote a piperazin-1-yl group which is substituted in the 4-position by a methyl group; and A denotes a methylene group; and their pharmacologically-acceptable acid-addition salts.

Illustrative examples of compounds according to the invention are:

4-(4-bromo)butyryl-3-chloro-9,10-dihydro-1-methyl-4H-thieno[3,4-b][1,5]benzodiazepin-10-one, 9,10-dihydro-1-ethyl-4-(2-chloro)propionyl-3-methyl-4H-thieno[3,4-b][1,5]benzodiazepin-10-one, 9,10-dihydro-1,3-dipropyl-4-[4-(N-methyl-N-propylamino)butyryl]-4H-thieno[3,4-b][1,5]benzodiazepin-10-one, 4-[5-(diethylamino)valeryl]-9,10-dihydro-3-ethyl-1-isopropyl-4H-thieno[3,4-b][1,5]benzodiazepin-10-one, 4-[5-(N-butyl-N-propylamino)valeryl]-9,10-dihydro-4H-thieno[3,4-b][1,5]benzodiazepin-10-one, 3-bromo-1-(n-butyl)-9,10-dihydro-4-diisopropylaminoacetyl-4H-thieno[3,4-b][1,5]benzodiazepin-10-one, 4-[(4-diallylamino)butyryl]-9,10-dihydro-1-ethyl-4H-thieno[3,4-b][1,5]benzodiazepin-10-one, 9,10-dihydro-1,3-dipropyl-4-[3-(N-methallyl-N-methylamino)-propionyl]-4H-thieno[3,4-b][1,5]benzodiazepin-10-one, 3-chloro-9,10-dihydro-1-isopropyl-4-(5-morpholinovaleryl)-4H-thieno[3,4-b][1,5]benzodiazepin-10-one, 1-butyl-9,10-dihydro-4-pyrrolidinoacetyl-4H-thieno[3,4-b][1,5]benzodiazepin-10-one, 9,10-dihydro-1,3-dimethyl-4-(3-piperidinopropionyl)-4H-thieno[3,4-b][1,5]benzodiazepin-10-one, 1,3-diethyl-9,10-dihydro-4-[(4-hexahydroazepin-1-yl)butyryl]-4H-thieno[3,4-b][1,5]benzodiazepin-10-one, 3-bromo-9,10-dihydro-1-methyl-4-[5-(4-methylpiperazin-1-yl)valeryl]-4H-thieno[3,4-b][1,5]benzodiazepin-10-one, 9,10-dihydro-4-[2-(4-ethylpiperazin-1-yl)propionyl]-4H-thieno[3,4-b][1,5]benzodiazepin-10-one, 4-[(4-benzylpiperazin-1-yl)acetyl]-1-butyl-9,10-dihydro-3-isopropyl-4H-thieno[3,4-b][1,5]benzodiazepin-10-one, 9,10-dihydro-1-isopropyl-3-methyl-4-[3-(4-methylhexahydro-1H-1,4-diazepin-1-yl)propionyl]-4H-thieno[3,4-b][1,5]benzodiazepin-10-one, 9,10-dihydro-1-ethyl-4-[4-(4-ethylhexahydro-1H-1,4-diazepin-1-yl)butyryl]-4H-thieno[3,4-b][1,5]benzodiazepin-10-one, 9,10-dihydro-4-[2-{di-(n-propyl)amino}propionyl]-4H-thieno[3,4-b][1,5]benzodiazepin-10-one, 4-[4-{di-(n-butyl)amino}butyryl]-9,10-dihydro-4H-thieno[3,4-b][1,5]benzodiazepin-10-one, 4-[2-(diethylamino)propionyl]-9,10-dihydro-4H-thieno[3,4-b][1,5]benzodiazepin-10-one, 4-[5-(diisopropylamino)valeryl]-9,10-dihydro-4H-thieno[3,4-b][1,5]benzodiazepin-10-one, 4-[diisobutylaminoacetyl]-9,10-dihydro-3-methyl-4H-thieno[3,4-b][1,5]benzodiazepin-10-one, 4-[N-(n-butyl)-N-(tert.-butyl)aminoacetyl]-9,10-dihydro-3-methyl-4H-thieno[3,4-b][1,5]benzodiazepin-10-one, 4-[4-(diallylamino)butyryl]-9,10-dihydro-1,3-dimethyl-4H-thieno[3,4-b][1,5]benzodiazepin-10-one, 4-[di-(sec.-butyl)aminoacetyl]-9,10-dihydro-4H-thieno[3,4-b][1,5]benzodiazepin-10-one, 4-[2-{N-ethyl-N-(n-butyl)amino}propionyl]-9,10-dihydro-4H-thieno[3,4-b][1,5]benzodiazepin-10-one, 9,10-dihydro-3-methyl-4-[N-methyl-N-(sec.-butyl)aminoacetyl]-4H-thieno[3,4-b][1,5]benzodiazepin-10-one, 9,10-dihydro-4-[5-{N-methyl-N-(tert.-butyl)amino}-valeryl]-4H-thieno[3,4-b][1,5]benzodiazepin-10-one, 9,10-dihydro-4-[2-piperidinopropionyl]-4H-thieno[3,4-b][1,5]benzodiazepin-10-one, 4-[4-(hexahydroazepin-1-yl)butyryl]-9,10-dihydro-4H-thieno[3,4-b][1,5]benzodiazepin-10-one, 4-[3-{di-(n-butyl)amino}propionyl]-9,10-dihydro-4H-thieno[3,4-b][1,5]benzodiazepin-10-one, 4-[3-(diallylamino)propionyl]-9,10-dihydro-B 4H-thieno[3,4-b][1,5]benzodiazepin-10-one, 4-[3-{di-(sec.-butyl)amino}propionyl]-9,10-dihydro-4H-thieno[3,4-b][1,5]benzodiazepin-10-one, 4-[3-{N-(n-butyl)-N-(tert.-butyl)amino}propionyl]-9,10-dihydro-4H-thieno[3,4-b][1,5]benzodiazepin-10-one, 4-[3-{(N-ethyl)-N-(n-butyl)amino}propionyl]-9,10-dihydro-4H-thieno[3,4-b][1,5]benzodiazepin-10-one, 9,10-dihydro-4-[3-{(N-methyl)-N-(sec.-butyl)amino}-propionyl]-4H-thieno [3,4-b][1,5]benzodiazepin-10-one, 9,10-dihydro-4-[3-piperidinopropionyl]-4H-thieno[3,4-b][1,5]benzodiazepin-10-one, 9,10-dihydro-3-methyl-4-[(4-methylpiperazin-1-yl)acetyl]-4H-thieno[3,4-b][1,5]benzodiazepin-10-one, 9,10-dihydro-1-methyl-4-[(4-methylpiperazin-1-yl)acetyl]-4H-thieno[3,4-b][1,5]benzodiazepin-10-one, 4-[3-(hexahydroazepin-1-yl)propionyl]-9,10-dihydro-4H-thieno[3,4-b][1,5]benzodiazepin-10-one and, preferably, 9,10-dihydro-4-[(4-methylpiperazin-1-yl)acetyl]-4H-thieno[3,4-b][1,5]benzodiazepin-10-one.

The substituted thienobenzodiazepinones of formula I and their acid-addition salts and embodiments I* and I have valuable properties which render them commercially useful. The substituted thienobenzodiazepinones of formula I [in which $R^3$ denotes —N($R^4$)$R^5$ and $R^4$ and $R^5$ have the previously-ascribed meanings] and those of embodiment I are characterized by excellent protective action on the stomach and intestines of warm-blooded animals; they inhibit, e.g., the development of gastric ulcers. Furthermore, as a result of their low toxicity and the absence of substantial side effects, they have an advantageous therapeutic range. The substituted thienobenzodiazepinones of formula I [in which $R^3$ denotes a halogen atom (Hal), and A and Hal have the previously-noted meanings] and those of embodiment I* are valuable intermediate products in the preparation of the pharmacologically-active and therapeutically-useful compounds according to the invention.

The excellent activity of the pharmacologically-active substituted thienobenzodiazepinones and their pharmacologically-, that is to say biologically-, acceptable acid-addition salts enables them to be employed in medicine, where they are used for the treatment and prophylaxis of disorders in the stomach of intestine and illnesses directly related thereto. Such illnesses include acute and chronic ulcus ventriculi and ulcus duodeni, gastritis and hyperacid gastric irritation in mammals.

The invention thus also relates to a process for treating mammals suffering from one of the noted illnesses. The process is characterized by administering a therapeutically-effective and pharmacologically-acceptable amount of one or more compounds of formula I (including compounds I**, preferred representatives thereof and/or salts thereof) to a sick mammal thus afflicted.

The invention also relates to the use of compounds according to the invention in combating the indicated illnesses. The invention furthermore comprises the use of compounds according to the invention in the preparation of medicaments which are employed for combating the mentioned illnesses.

The invention also relates to medicaments which contain one or more thienobenzodiazepinones Ia of formula I, wherein $R^1$ denotes a hydrogen atom (—H) or an alkyl radical with from 1 to 4 carbon atoms, $R^2$ represents a halogen atom (halo) or has one of the meanings of $R^1$, $R^3$ denotes —N($R^4$)$R^5$, $R^4$ denotes an alkyl radical with from 1 to 4 carbon atoms, an alkenyl radical with from 3 to 5 carbon atoms or, together with $R^5$ and the nitrogen atom to which both are bound, a morpholino group, a pyrrolidino group, a piperidino group, a hexahydroazepin-1-yl group, a piperazin-1-yl group (which is optionally substituted in the 4-position by a methyl or ethyl group or by a benzyl group), a 2,4-dimethylpiperazin-1-yl group, or a hexahydro-1H-1,4-diazepin-1-yl group which is substituted in the 4-position by a methyl or ethyl group, $R^5$ has one of the meanings of $R^4$, represents —(CH$_2$)$_m$—N($R^6$)$R^7$ or, together with $R^4$ and the nitrogen atom to which both are bound, denotes a morpholino group, a pyrrolidino group, a piperidino group, a hexahydroazepin-1-yl group, a piperazin-1-yl group (which is optionally substituted in the 4-position by a methyl or ethyl group or by a benzyl group), a 2,4-dimethylpiperazin-1-yl group, or a hexahydro-1H-1,4-diazepin-1-yl group which is substituted in the 4-position by a methyl or ethyl group, $R^6$ denotes an alkyl group with from 1 to 4 carbon atoms, $R^7$ denotes an alkyl group with from 1 to 4 carbon atoms, A denotes a straight-chain or branched alkylene group with from 1 to 5 carbon atoms and m denotes 2 or 3, and/or their pharmacologically-acceptable acid-addition salts.

Embodiments of the medicaments comprise, e.g., thienobenzodiazepinones I** or their preferred representatives and/or their pharmacologically-acceptable acid-addition salts.

The medicaments are prepared by standard recognized processes. As medicaments, the compounds according to the invention are employed either on their own or, preferably, in combination with suitable known pharmaceutical excipients. When the new pharmaceutical formulations contain pharmaceutical excipients in addition to one or more compounds according to the invention, the content of active compound in the resulting compositions is from 0.5 to 95, preferably 15 to 75, percent by weight of the total.

In accordance with the invention the active compounds are used (in the field of medicine) in any form suitable to establish and/or maintain a sufficient blood and tissue level of active compound. This is achieved, for example, by oral, rectal or parenteral administration in suitable doses. The pharmaceutical formulation of active compound is usually in the form of unit doses appropriate for the desired administration. A unit dose is, for example, a tablet, a dragee, a capsule, a suppository or a measured volume of a powder, of a granular material, of a solution, of an emulsion or of a suspension.

"Unit dose" in the context of the present invention means a physically-determined unit which contains an individual amount of active ingredient in combination with a pharmaceutical excipient, the content of active compound in the unit dose corresponding to a fraction or multiple of a therapeutic individual dose. An individual dose preferably contains the amount of active compound which is given in one administration and usually corresponds to a whole daily dose or a half, one-third or one-quarter of the daily dose. If only a fraction, such as a half or one-quarter, of the unit dose is required for an individual therapeutic administration, the unit dose is advantageously divisible, for example in the form of a tablet with a breaking groove.

When in the form of unit doses and intended, for example, for administration to mammals, the pharmaceutical formulations according to the invention contain, e.g., from about 0.1 to 500 mg (advantageously from 0.5 to 100 mg and, in particular, from 1 to 30 mg) of active compound.

It is advantageous in medicine to administer the active compound or compounds (when these are given orally) in a daily dose of from about 0.01 to about 5, preferably from 0.05 to 2.5 and, in particular, from 0.1 to 1.5, mg/kg of body weight, generally in the form of several, preferably 1 to 3, individual administrations in order to achieve the desired results. An individual administration contains the active compound or compounds in an amount of from about 0.01 to about 2.5, preferably from 0.01 to 1.5 and, in particular, from 0.05 to 0.5, mg/kg of body weight. Similar dosages are used for parenteral, for example intravenous, treatment.

The therapeutic administration of the pharmaceutical formulation is effected 1 to 4 times daily at fixed or varying points in time, for example before each meal and/or in the evening. However, it may be necessary to deviate from the mentioned dosages in view of the condition, body weight and age of the individual to be treated, the nature and severity of the illness, the nature of the formulation and of the administration of the medicament, the frequency of administration and the time or interval over which administration takes place. Thus, in some cases less than the suggested amount of active compound is sufficient, whereas the indicated amount of active compound must be exceeded in other cases.

The optimum dosage and method of administration of the active compounds required in each particular case are readily determined by those of ordinary skill in the art on the basis of their expertise.

The pharmaceutical formulations preferably comprise an active compound according to the invention and non-toxic, pharmaceutically-acceptable medicinal excipients (which are used as an admixture or diluent in solid, semi-solid or liquid form, or as a means of encasing, for example in the form of a capsule, a tablet coating, a sachet or some other container for the therapeutically-active ingredient). An excipient optionally serves as a promoter of the resorption of the medicament by the body, as a formulating auxiliary, as a sweetener, as a flavor correctant, as a colorant or as a preservative.

Examples of oral dosage forms are tablets, dragees, hard and soft capsules, for example made of gelatin, dispersible powders, granules, aqueous and oily suspensions, emulsions, solutions or syrups.

Tablets contain inert diluents, for example calcium carbonate, calcium phosphate, sodium phosphate or lactose; granulating agents and dispersing agents, for example maize starch or alginates; binders, for example starch, gelatin or gum acacia; and lubricants, for example aluminum stearate or magnesium stearate, talc or silicone oil. The tablets are optionally provided with a coating. Delayed dissolution and resorption of the medicament in the gastrointestinal tract and hence, for example, better toleration, a protracted effect or a delayed effect are optionally achieved by tablet coatings. Gelatin capsules generally contain the medicament mixed with a diluent, for example a solid diluent, such as calcium carbonate or kaolin, or an oily diluent, such as neutral oil, olive oil, groundnut oil or paraffin oil.

Aqueous suspensions optionally contain suspending agents, for example sodium carboxymethylcellulose, methylcellulose, hydroxypropylcellulose, sodium alginate, polyvinylpyrrolidone, gum tragacanth or gum acacia; dispersing agents and wetting agents, for example polyoxyethylene stearate, heptadecaethyleneoxycetanol, polyoxyethylene sorbitol monooleate, polyoxyethylene sorbitan monooleate or lecithin; preservatives, for example methyl hydroxybenzoate or propyl hydroxybenzoate; flavoring agents; and sweeteners, for example sucrose, lactose, sodium cyclamate, dextrose or invert sugar syrup.

Oily suspensions contain, for example, groundnut oil, olive oil, sesame oil, coconut oil or paraffin oil, and thickeners, such as beeswax, hard paraffin or cetyl alcohol; and, furthermore, sweeteners, flavoring agents and antioxidants.

Emulsions contain, for example, olive oil, groundnut oil or paraffin oil, in addition to emulsifying agents, such as gum acacia, gum tragacanth, phosphatides, sorbitan monooleate or polyoxyethylene sorbitan monooleate, and sweeteners and flavoring agents.

For rectal administration of the medicaments, suppositories, which are prepared with the aid of binders (which melt at rectal temperature), for example cacao butter or polyethylene glycol, are used.

For parenteral administration of the medicaments, sterile injectable aqueous suspensions, isotonic salt solutions or other solutions which contain dispersing agents or wetting agents and/or pharmacologically-acceptable diluents, for example propylene glycol or butylene glycol, are used.

The active compound or compounds are alternatively formulated in a micro-encapsulated form, optionally with the addition of the mentioned excipients or additives.

When the substituted thienobenzodiazepinones according to the invention and/or their pharmacologically-acceptable acid-addition salts are employed for treating the stated illnesses, the pharmaceutical formulations optionally also contain one or more pharmacologically-active ingredients from other groups of medicaments, such as antacids, for example aluminum hydroxide and magnesium aluminate; secretion inhibitors, such as $H_2$-blockers, for example cimetidine; gastric and intestinal therapeutics, for example metoclopramide, bromopride and tiapride; tranquilizers, such as benzodiazepines, for example diazepam; spasmolytic agents, for example bietamiverine and camylofin; anticholinergic agents, for example oxyphencyclimine and phencarbamide; glucocorticoids, such as prednisolone, fluocortolone and betamethasone; nonsteroidal antiphlogistic agents, such as arylacetic acids and arylpropionic acids and heteroarylacetic acids and hetero-arylpropionic acids, benzothiazinecarboxamide dioxides, pyrazolidinediones and quinazolinones, for example ibuprofen, naproxen, diclofenac, fenbufen, indomethacin, lonazolac, sudoxicam, piroxicam, phenylbutazone, bumadizone calcium and proquazone; and local anaesthetics, for example tetracaine and procaine; and, if appropriate, also enzymes, vitamins, aminoacids and the like.

The invention furthermore relates to a process for the preparation of the substituted thienobenzodiazepinones of formula I, wherein $R^1$ denotes a hydrogen atom (-H) or an alkyl radical with from 1 to 4 carbon atoms, $R^2$ represents a halogen atom (halo) or has one of the meanings of $R^1$, $R^3$ denotes a halogen atom (halo) or —$N(R^4)R^5$, $R^4$ denotes an alkyl radical with from 1 to 4 carbon atoms, an alkenyl radical with from 3 to 5 carbon atoms or, together with $R^5$ and the nitrogen atom to which both are bound, a morpholino group, a pyrrolidino group, a piperidino group, a hexahydroazepin-1-yl group, a piperazin-1-yl group (which is optionally substituted in the 4-position by a methyl or ethyl group or by a benzyl group), a 2,4-dimethylpiperazin-1-yl group, or a hexahydro-1H-1,4-diazepin-1-yl group which is substituted in the 4-position by a methyl or ethyl group, $R^5$ has one of the meanings of $R^4$, represents —$(CH_2)_m$—$N(R^6)R^7$ or together with $R^4$ and the nitrogen atom to which both are bound, denotes a morpholino group, a pyrrolidino group, a piperidino group, a hexahydroazepin-1-yl group, a piperazin-1-yl group (which is optionally substituted in the 4-position by a methyl or ethyl group or by a benzyl group), a 2,4-dimethylpiperazin-1-yl group, or a hexahydro-1H-1,4-diazepin-1-yl group which is substituted in the 4-position by a methyl or ethyl group, $R^6$ denotes an alkyl group with from 1 to 4 carbon atoms, $R^7$ denotes an alkyl group with from 1 to 4 carbon atoms, A denotes a straight-chain or branched alkylene group with from 1 to 5 carbon atoms and m denotes 2 or 3, and their acid-addition salts.

The process is characterized by acylating a thienobenzodiazepinone of the formula

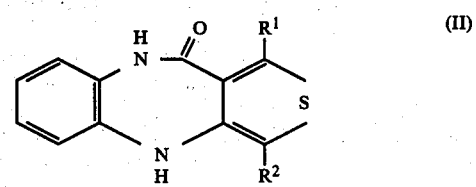

(wherein $R^1$ and $R^2$ have their previously-ascribed meanings) and, if desired, aminating thereafter. Resulting free bases (products having a basic nitrogen) are optionally converted into acid-addition salts; resulting acid-addition salts are optionally converted into corresponding free bases or into other and pharmacologically-acceptable acid-addition salts.

The acylation and the subsequent optional amination are carried out by well-established conventional methods.

To prepare the thienobenzodiazepinones of formula I in which $R^3$ denotes Hal, the starting compounds of formula II (wherein $R^1$ and $R^2$ have their previously-noted meanings) or their acid-addition salts are reacted with a compound of the formula: Hal-A-CO-Hal' (III) or one of the formula: [Hal-A-CO]$_2$O (IV), wherein Hal' has one of the meanings of Hal, and A and Hal have their indicated meanings. This acylation is carried out without a solvent or, preferably, in an inert solvent at room temperature (20° C.) or elevated temperature, the maximum temperature being the boiling point of the solvent; the acylation reaction mixture optionally comprises an auxiliary base and/or an acylation catalyst. The acid halides III are preferred over the acid anhydrides IV. Chloroacetyl chloride is the preferred acid halide III and chloroacetic anhydride is the preferred acid anhydride IV. Examples of suitable solvents are aromatic hydrocarbons, such as toluene, xylene or chlorobenzene; open-chain or cyclic ethers, such as diisopropyl ether or dioxane; chlorinated hydrocarbons, such as dichloroethane, and other solvents, such as pyridine, acetonitrile or dimethylformamide. Illustrative auxiliary bases are, for example, tertiary organic bases, such as triethylamine and ethyl diisopropylamine, or pyridine; or inorganic bases, such as anhydrous alkali-metal carbonates or bicarbonates or alkaline-earth-metal carbonates or bicarbonates or alkaline-earth-metal oxides. Exemplary acylation catalysts are imidazole, pyridine or 4-dimethylaminopyridine.

The process for the preparation of intermediate products of formula I is thus characterized by acylating a thienobenzodiazepinone of formula II with a compound of formula III or of formula IV. Corresponding starting substances are employed for the preparation of intermediate products I*.

To alternatively prepare the thienbenzodiazepinones of formula I in which $R^2$ and $R^3$ denote Hal, the starting compounds of formula II (wherein $R^1$ has its previously-noted meaning) or their acid-addition salts are reacted with a compound of the formula: Hal-A-CO-Hal' (III) or one of the formula: [Hal-A-CO]$_2$O (IV), wherein Hal' has one of the meanings of Hal, and A and Hal have their indicated meanings, and are subsequently chlorinated or brominated. This halogenation is carried out, e.g., with a suitable halogenating agent, such as sulfuryl chloride or bromide, in an inert solvent at temperatures between $-20°$ to $50°$ C., preferably at room temperature (20° C.). Examples of suitable solvents are chlorinated hydrocarbons, such as dichloroethane or methylene chloride.

The alternative process for the preparation of intermediate products of formula I (wherein $R^2$ is halo) is thus characterized by acylating a thienbenzodiazepinone of formula II (wherein $R^2$ is hydrogen) with a compound of formula III or of formula IV and subsequently halogenating. Corresponding starting substances are employed for the preparation of intermediate products I*.

To prepare the substitited thienobenzodiazepinones of formula I in which $R^1$ and $R^2$ have their noted meanings and $R^3$ denotes $-N(R^4)R^5$, the resulting reaction product of formula I (wherein $R^3$ denotes Hal) is reacted with a secondary amine of the formula: $HN(R^4)R^5$ (V), wherein $R^4$, $R^5$ and Hal have their previously-ascribed meanings.

The amination is carried out in an inert solvent at temperatures between 0° C. and the boiling point of the solvent (either with at least 2 mols of secondary amine V or with from 1 to 2 mols of secondary amine V and an auxiliary base). Suitable solvents are, e.g., chlorinated hydrocarbons, such as methylene chloride, chloroform or dichloroethane; open-chain or cyclic ethers, such as diethyl ether, tetrahydrofuran or dioxane; aromatic hydrocarbons, such as benzene, toluene, xylene, chlorobenzene or pyridine; alcohols, such as ethanol or isopropanol; ketones, such as acetone; acetonitrile or dimethylformamide. Suitable auxiliary bases include, e.g., teriary organic bases, such as triethylamine, N-methylpiperidine, diethylaniline or pyridine, or inorganic bases, such as alkali-metal carbonates or bicarbonates or alkaline-earth-metal carbonates or bicarbonates or alkaline-earth-metal hydroxides or oxides. The reaction is optionally accelerated by incorporating alkali-metal iodide in the reaction medium. The reaction time is from 15 minutes to 80 hours, depending on the amount and nature of the amine V employed. When starting compounds in which A represents an alkylene group with from 2 to 5 carbon atoms are reacted, the reaction alternatively proceeds with H-Hal being split off; the intermediately-formed alkenyl compound, which is optionally isolated, reacts with the secondary amine V to yield the same end product.

The process for the preparation of the pharmacologically-active thienobenzodiazepinones of formula I is thus characterized by reacting compounds of formula I (wherein $R_3$ denotes Hal) with compounds of formula V and, when appropriate, converting the resulting base into a pharmacologically-acceptable acid-addition salt, or converting a resulting acid-addition salt into the free base or into a different and pharmacologically-acceptable acid-addition salt.

Acid-addition salts are obtained by dissolving the resulting free base in a suitable solvent, for example water, acetone, an alkanol (such as ethanol or isopropanol) or an open-chain or cyclic ether (such as diethyl ether or tetrahydrofurane), which contains the desired acid or to which the desired acid is then added. The salts are isolated by filtration, precipitation with a nonsolvent for the acid-addition salt or by evaporation of the solvent. Salts can also be converted into other salts, for example pharmacologically-acceptable acid-addition salts, by converting them first into the free base and then reacting the base further with another acid.

Resulting salts are converted into the free base, for example, by alkalization with aqueous sodium hydroxide or potassium hydroxide; the free base is then isolated by suitable measures, for example solvent extraction with a water-immiscible solvent, such as chloroform, diethyl ether or toluene.

The preparation of the starting compounds of the formula II is carried out according to or analogously with the preparation in U.S. Pat. No. 3,953,430, in accordance with the following reaction scheme:

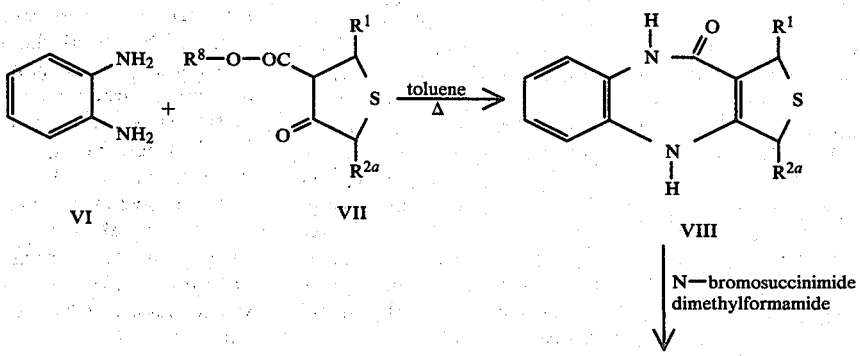

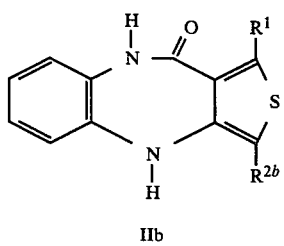

IIb

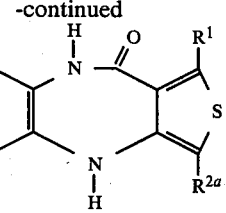

IIa

Phenylenediamine VI is reacted (while heating) with a tetrahydrothiophenecarboxylic acid derivative VII [in which $R^1$ has its previously-stated meaning, $R^{2a}$ denotes a hydrogen atom (—H) or an alkyl group with from 1 to 4 carbon atoms and $R^8$ denotes a hydrogen atom (—H) or an alkyl group with from 1 to 5 carbon atoms] in inert solvent, for example toluene, to form the corresponding tetrahydrothienobenzodiazepinone VIII. Compounds VIII are dehydrogenated with a suitable dehydrogenating agent, for example N-bromosuccinimide in dimethylformamide, to give the dihydrothienobenzodiazepinones IIa. The representatives IIa, in which $R^{2a}$ denotes a hydrogen atom, are converted into halogen derivatives IIb, in which $R^{2b}$ denotes a chlorine or bromine atom, by chlorination or bromination with a suitable halogenating agent.

Corresponding starting compounds II*, II**, III*, III**, IV*, IV and V are employed for the preparation of embodiments I* and I**.

The following examples, wherein "m." denotes "melting point", serve to illustrate the invention in more detail.

EXAMPLE 1

3.5 g of 4-chloroacetyl-9,10-dihydro-4H-thieno[3,4-b][1,5]benzodiazepin-10-one, 8.1 g of N-methylpiperazine and 50 ml of toluene are stirred at 80° C. for 2 hours. 60 ml of dilute sodium hydroxide solution are added; the resulting layers (an aqueous phase and an organic phase) are separated; the aqueous phase is extracted several times by shaking it with toluene. It is then concentrated to dryness in vacuo. The obtained residue is made to crystallize with a little acetone. 4.2 g of 9,10-dihydro-4-[(4-methylpiperazin-1-yl)acetyl]-4H-thieno[3,4-b][1,5]benzodiazepin-10-one, m. 177° to 178° C. (acetone), are thus obtained.

9,10-Dihydro-3-methyl-4-[(4-methylpiperazin-1-yl)acetyl]-4H-thieno[3,4-b][1,5]benzodiazepin-10-one, m. 263° to 264° C. (ethanol), 3-chloro-9,10-dihydro-4-[(4-methylpiperazin-1-yl)acetyl]-4H-thieno[3,4-b][1,5]benzodiazepin-10-one (m. 239° C.) and 9,10-dihydro-1,3-dimethyl-4-[(4-methylpiperazin-1-yl)acetyl]-4H-thieno[3,4-b][1,5]benzodiazepin-10-one (m. 204° to 205° C.) are obtained analogously by reacting corresponding amounts of 4-chloroacetyl-9,10-dihydro-3-methyl-4H-thieno[3,4-b][1,5]benzodiazepin-10-one, 3-chloro-4-chloroacetyl-9,10-dihydro-4H-thieno[3,4-b][1,5]benzodiazepin-10-one or 4-chloroacetyl-9,10-dihydro-1,3-dimethyl-4H-thieno[3,4-b][1,5]benzodiazepin-10-one (instead of 4-chloroacetyl-9,10-dihydro-4H-thieno[3,4-b][1,5]benzodiazepin-10-one) with N-methylpiperazine.

EXAMPLE 2

14.9 g of 4-chloroacetyl-9,10-dihydro-4H-thieno[3,4-b][1,5]benzodiazepin-10-one, 21 g of N-methylpiperazine and 70 ml of dioxane are stirred at 80° C. for 1 hour, and the obtained solution is concentrated to dryness in vacuo. 150 ml of isopropanol and 40 ml of water are added to the resulting residue, and 25 ml of concentrated hydrochloric acid are then added dropwise; the thus prepared mixture is cooled in an ice-bath, and 9,10-dihydro-4-[(4-methylpiperazin-1-yl)acetyl]-4H-thieno[3,4-b][1,5]benzodiazepin-10-one dihydrochloride is obtained as a mixture with N-methylpiperazine hydrochloride. The hydrochlorides are dissolved in water and chloroform; the pH is adjusted to 8.2 with 2 N sodium hydroxide solution; the aqueous phase is extracted exhaustively by shaking it with chloroform, and the organic solution is dried and concentrated to dryness in vacuo. 16 g of 9,10-dihydro-4-[(4-methylpiperazin-1-yl)acetyl]-4H-thieno[3,4-b][1,5]benzodiazepin-10-one, m. 177° to 178° C. (from acetone), are thus obtained.

9,10-Dihydro-4-(morpholinoacetyl)-4H-thieno[3,4-b][1,5]benzodiazepin-10-one, 4-[(4-benzylpiperazin-1-yl)acetyl]-9,10-dihydro-4H-thieno[3,4-b][1,5]benzodiazepin-10-one, 4-[(4-ethylpiperazin-1-yl)acetyl]-9,10-dihydro-4H-thieno[3,4-b][1,5]benzodiazepin-10-one and 4-[(2,4-dimethylpiperazin-1-yl)acetyl]-9,10-dihydro-4H-thieno[3,4-b][1,5]benzodiazepin-10-one are obtained analogously by reacting 4-chloroacetyl-9,10-dihydro-4H-thieno[3,4-b][1,5]benzodiazepin-10-one with corresponding amounts of morpholine, N-benzylpiperazine, N-ethylpiperazine and 1,3-dimethylpiperazine, respectively.

EXAMPLE 3

1.9 g of 4-chloroacetyl-9,10-dihydro-4H-thieno[3,4-b][1,5]benzodiazepin-10-one, 0.55 g of pyrrolidine, 0.85 g of ground sodium carbonate and 15 ml of absolute ethanol are heated at the boil for 2 hours, and the resulting hot solution is filtered and concentrated in vacuo. The obtained residue is dissolved in methylene chloride; the organic solution is washed at pH 7 with water and then concentrated; 1.4 g of 9,10-dihydro-4-(pyrrolidinoacetyl)-4H-thieno[3,4-b][1,5]benzodiazepin-10-one are thus obtained.

EXAMPLE 4

1.9 g of 4-chloroacetyl-9,10-dihydro-4H-thieno[3,4-b][1,5]benzodiazepin-10-one, 3.7 g of piperidine and 15 ml of dioxane are stirred at 80° C. for 1 hour; the resulting mixture is concentrated in vacuo, and the obtained residue is recrystallized from isopropanol/water. 2.0 g of 9,10-dihydro-4-(piperidinoacetyl)-4H-thieno[3,4-b][1,5]benzodiazepin-10-one are thus obtained.

EXAMPLE 5

2.0 g of 4-chloroacetyl-9,10-dihydro-4H-thieno[3,4-b][1,5]benzodiazepin-10-one, 6 ml of 40% strength aqueous dimethylamine solution and 10 ml of methylene chloride are stirred at 35° C. for 2 hours; 0.35 g of sodium carbonate is added, and the mixture is concentrated to dryness in vacuo. A little water is added; the solution is extracted repeatedly by shaking it with chloroform, and the organic solution is dried with sodium sulfate and concentrated to dryness. 1.9 g of 4-(dimethylaminoacetyl)-9,10-dihydro-4H-thieno[3,4-b][1,5]benzodiazepin-10-one are thus obtained. 4-(Diethylaminoacetyl)-9,10-dihydro-3-methyl-4H-thieno[3,4-b][1,5]benzodiazepin-10-one [m. 196°–197° C. (from toluene)] is obtained analogously by reacting 4-chloroacetyl-9,10-dihydro-3-methyl-4H-thieno[3,4-b][1,5]benzodiazepin-10-one with a corresponding amount of diethylamine (instead of dimethylamine).

EXAMPLE 6

9,10-Dihydro-3-methyl-4-(pyrrolidinoacetyl)-4H-thieno[3,4-b][1,5]benzodiazepin-10-one, 3-chloro-9,10-dihydro-4-(pyrrolidinoacetyl)-4H-thieno[3,4-b][1,5]benzodiazepin-10-one and 9,10-dihydro-1,3-dimethyl-4-(pyrrolidinoacetyl)-4H-thieno[3,4-b][1,5]benzodiazepin-10-one are obtained analogously to the procedure of Example 4 by reacting corresponding amounts (instead of 4-chloroacetyl-9,10-dihydro-4H-thieno[3,4-b][1,5]benzodiazepin-10-one) of 4-chloroacetyl-9,10-dihydro-3-methyl-4H-thieno[3,4-b][1,5]benzodiazepin-10-one, 3-chloro-4-chloroacetyl-9,10-dihydro-4H-thieno[3,4-b][1,5]benzodiazepin-10-one and 4-chloroacetyl-9,10-dihydro-1,3-dimethyl-4H-thieno[3,4-b][1,5]benzodiazepin-10-one, respectively, with pyrrolidine.

EXAMPLE 7

4-(Dimethylaminoacetyl)-9,10-dihydro-3-methyl-4H-thieno[3,4-b][1,5]benzodiazepin-10-one, 3-chloro-4-(dimethylaminoacetyl)-9,10-dihydro-4H-thieno[3,4-b][1,5]benzodiazepin-10-one and 4-(dimethylaminoacetyl)-9,10-dihydro-1,3-dimethyl-4H-thieno[3,4-b][1,5]benzodiazepin-10-one are obtained analogously to the procedure of Example 5 by reacting corresponding amounts (instead of 4-chloroacetyl-9,10-dihydro-4H-thieno[3,4-b][1,5]benzodiazepin-10-one) of 4-chloroacetyl-9,10-dihydro-3-methyl-4H-thieno[3,4-b][1,5]benzodiazepin-10-one, 3-chloro-4-chloroacetyl-9,10-dihydro-4H-thieno[3,4-b][1,5]benzodiazepin-10-one and 4-chloroacetyl-9,10-dihydro-1,3-dimethyl-4H-thieno[3,4-b][1,5]benzodiazepin-10-one, respectively, with dimethylamine.

EXAMPLE 8

8 g of 9,10-dihydro-3-methyl-4H-thieno[3,4-b][1,5]benzodiazepin-10-one and 5.6 ml of chloroacetyl chloride are boiled in 160 ml of dioxane (containing 8 g of ground potassium carbonate) under reflux for 8 hours. The thus-obtained suspension is concentrated to dryness; the resulting residue is taken up in toluene; the toluene mixture is washed with sodium bicarbonate solution and then with water, and the toluene solution is dried over sodium sulfate. Concentration of the dried toluene solution yields 4-chloroacetyl-9,10-dihydro-3-methyl-4H-thieno[3,4-b][1,5]benzodiazepin-10-one (m. 156° to 158° C.).

3-Chloro-4-chloroacetyl-9,10-dihydro-4H-thieno[3,4-b][1,5]benzodiazepin-10-one (m. 214° to 216° C.) and 4-chloroacetyl-9,10-dihydro-1,3-dimethyl-4H-thieno[3,4-b][1,5]benzodiazepin-10-one (m. 192°–195° C.) are obtained analogously by reacting corresponding amounts (instead of 9,10-dihydro-3-methyl-4H-thieno[3,4-b][1,5]benzodiazepin-10-one) of 3-chloro-9,10-dihydro-4H-thieno[3,4-b][1,5]benzodiazepin-10-one and 9,10-dihydro-1,3-dimethyl-4H-thieno[3,4-b][1,5]benzodiazepin-10-one, respectively, with chloroacetyl chloride.

EXAMPLE 9

10.4 ml of chloroacetyl chloride are added dropwise at room temperature to a suspension of 18.8 g of 9,10-dihydro-4H-thieno[3,4-b][1,5]benzodiazepin-10-one in 500 ml of dioxane, whereupon a clear solution is formed. The solution is left to stand for 3 hours and is then concentrated to dryness; the obtained residue is taken up in toluene; the toluene mixture is washed with sodium bicarbonate solution and then with water, and the toluene solution is dried over sodium sulfate. Concentration of the thus-dried solution yields 4-chloroacetyl-9,10-dihydro-4H-thieno[3,4-b][1,5]benzodiazepin-10-one (m. 220° C.).

4-Chloroacetyl-9,10-dihydro-1-methyl-4H-thieno[3,4-b][1,5]benzodiazepin-10-one and 4-Chloroacetyl-9,10-dihydro-3-methyl-4H-thieno[3,4-b][1,5]benzodiazepin-10-one, respectively, are obtained analogously by reacting corresponding amounts (instead of 9,10-dihydro-4H-thieno[3,4-b][1,5]benzodiazepin-10-one) of 9,10-dihydro-1-methyl-4H-thieno[3,4-b][1,5]benzodiazepin-10-one and 9,10-dihydro-3-methyl-4H-thieno[3,4-b][1,5]benzodiazepin-10-one, respectively, with chloroacetyl chloride.

EXAMPLE 10

2.2 g of chloroacetyl chloride and 2 ml of triethylamine are simultaneously added dropwise to a boiling solution of 2.2 g of 9,10-dihydro-4H-thieno[3,4-b][1,5]benzodiazepin-10-one in 30 ml of absolute dioxane in the course of 40 minutes, and the mixture is stirred for a further 3 hours. It is then allowed to cool and is filtered; the filtrate is concentrated to dryness; the residue is chromatographed over a silica gel column by means of a mixture of petroleum ether/ethyl acetate (1:1), and the product is recrystallized from toluene to yield 2.0 g of 4-chloroacetyl-9,10-dihydro-4H-thieno[3,4-b][1,5]benzodiazepin-10-one (m. 220° C.).

EXAMPLE 11

5 ml of sulfuryl chloride in 100 ml methylene chloride are added dropwise to a solution of 12 g of 4-chloroacetyl-9,10-dihydro-4H-thieno[3,4-b][1,5]benzodiazepin-10-one in 300 ml of methylene chloride at 20° C. The mixture is left to stand at room temperature for a further 12 hours and is then extracted by shaking it with sodium bicarbonate solution and washing it with water; the organic phase is dried and concentrated. The residue is made to crystallize with a little methanol. 7 g of 3-chloro-4-chloroacetyl-9,10-dihydro-4H-thieno[3,4-b][1,5]benzodiazepin-10-one is thus obtained, m. 214° to 216° C. (acetonitrile).

The starting compounds are obtained in the following manner:

Example A: 13.5 g of sulfuryl chloride in 100 ml of methylene chloride are added dropwise to a solution of 21.6 g of 9,10-dihydro-4H-thieno[3,4-b][1,5]benzodiazepin-10-one in 300 ml of methylene chloride at −40° C. The mixture is left to stand at room temperature for a further hour and is then extracted by shaking it with sodium bicarbonate solution and washing it with water; the organic phase is dried and concentrated. The residue is made to crystallize with a little methanol. 3-

Chloro-9,10-dihydro-4H-thieno[3,4-b][1,5]benzodiazepin-10-one is thus obtained.

Example B: 10 g of 1,3,9,10-tetrahydro-3-methyl-4H-thieno[3,4-b][1,5]benzodiazepin-10-one and 8.2 g of N-bromosuccinimide are dissolved in 250 ml of dimethylformamide. After one hour, the solution is poured into 2 l of water. The precipitate is filtered off and dissolved in hot toluene, and the solution is clarified with Tonsil ®. On cooling, 9,10-dihydro-3-methyl-4H-thieno[3,4-b][1,5]benzodiazepin-10-one, m. 228° to 230° C. (methanol), is thus obtained as a precipitate.

9,10-Dihydro-1-methyl-4H-thieno[3,4-b][1,5]benzodiazepin-10-one (m. 179° to 180° C.) and 9,10-dihydro-1,3-dimethyl-4H-thieno[3,4-b][1,5]benzodiazepin-10-one (m. 195° to 196° C.) are analogously obtained by dehydrogenating 1,3,9,10-tetrahydro-1-methyl-4H-thieno[3,4-b][1,5]benzodiazepin-10-one or 1,3,9,10-tetrahydro-1,3-dimethyl-4H-thieno[3,4-b][1,5]benzodiazepin-10-one with N-bromosuccinimide.

Example C: 49.9 g of 1,2-phenylenediamine and 80 g of 5-methyl-tetrahydro-4-oxo-3-thiophenecarboxylic acid are boiled in 4.5 l of toluene. The water formed is distilled off azeotropically with 2 l of the solvent in the course of 7 hours. The solvent is removed. 1,3,9,10-Tetrahydro-3-methyl-4H-thieno[3,4-b][1,5]benzodiazepin-10-one, m. 195° to 197° C. (isopropanol), is thus obtained.

1,3,9,10-Tetrahydro-1-methyl-4H-thieno[3,4-b][1,5]benzodiazepin-10-one (m. 156° to 157° C.) and 1,3,9,10-tetrahydro-1,3-dimethyl-4H-thieno[3,4-b][1,5]benzodiazepin-10-one (m. 148° to 150° C.) are analogously obtained by reacting tetrahydro-2-methyl-4-oxo-3-thiophenecarboxylic acid or tetrahydro-2,5-dimethyl-4-oxo-3-thiophenecarboxylic acid with 1,2-phenylenediamine.

The following examples describe the formulation of a compound according to the invention to give medicaments.

EXAMPLE 12

10,000 tablets with an active compound content of 20 mg are prepared from the following constituents: 200 g of 9,10-dihydro-4-[(4-methylpiperazin-1-yl)acetyl]-4H-thieno[3,4-b][1,5]benzodiazepin-10-one, 900 g of maize starch, 500 g of lactose, 30 g of amorphous silicic acid and 40 g of sodium lauryl-sulfate are mixed, and the mixture is sieved. This mixture is moistened with a solution of 50 g of polyvinylpyrrolidone (average molecular weight: 25,000) in 320 ml of ethanol and is granulated through a sieve (mesh width 1.25 mm). The granules are dried at 40° C. and mixed with 160 g of pectin, 100 g of talc and 20 g of magnesium stearate. This mixture is compressed to 200 mg tablets with a diameter of 8 mm.

EXAMPLE 13

100,000 capsules with an active compound content of 30 mg are prepared from the following constituents: 3,000 g of 9,10-dihydro-4-[(4-methylpiperazin-1-yl)acetyl]-4H-thieno[3,4-b][1,5]benzodiazepin-10-one are mixed with 5,000 g of neutral oil (Miglyol ® 812), and the mixture is filled into soft gelatin capsules.

EXAMPLE 14

100,000 capsules with an active compound content of 30 mg are prepared from the following constituents: 1,500 g of 9,10-dihydro-4-[(4-methylpiperazin-1-yl)acetyl]-4H-thieno[3,4-b][1,5]benzodiazepin-10-one and 1,500 g of magnesium trisilicate are mixed with 5,000 g of neutral oil (Miglyol ® 812), and the mixture is filled into soft gelatin capsules.

Pharmacology

The excellent protective action on the stomach shown by the pharmacologically-active substituted thienobenzodiazepinones is demonstrated using as a model the so-called Shay rat. The compounds according to the invention prove to have a protective action on the stomach and a therapeutic range which are clearly superior to those of the known commercial product, carbenoxolone (1), as is shown, for example, by comparing (1) with 9,10-dihydro-4-[(4-methylpiperazin-1-yl)acetyl]-4H-thieno[3,4-b][1,5]benzodiazepin-10-one (2).

TABLE I

Antiulcerogenic action and toxicity of thienobenzodiazepinones

| Serial No. | Toxicity $LD_{50}$[mg/kg], intravenous administration to mice | Protective action on the stomach $ED_{50}$[mg/kg], peroral administration to rats | TQ $LD_{50}/ED_{50}$ | Gastric secretion(+) % inhibition in rats |
|---|---|---|---|---|
| 1 | 290 | ~70 | 4.1 | 7 |
| 2 | 190 | 2.5 | 76 | 35 |

$ED_{50}$ = dose which reduces the ulcer index by 50% in the treated group compared with the control group
$LD_{50}$ = dose at which 50% of the animals die
TQ = therapeutic quotient $LD_{50}/ED_{50}$
(+)% inhibition = inhibition of the gastric secretion (in %) 4 hours after administration of the antiulcerogenic $ED_{50}$ It should be particularly emphasized that an $ED_{50}$ can indeed still be determined in the case of compound 1, but the dose/action curve is then very severely flattened so that no substantial increase in the ulcerogenic action can be achieved even at 300 mg/kg. In contrast, the action of compound 2 is strictly dependent on the dose; inhibition effects of up to 95% (10 mg/kg) can be achieved.

The antiulcerogenic action was tested in accordance with the method using the so-called Shay rat:

Rats (female, 180 to 200 g, 4 animals per cage on a high grid) which had been fasted for 24 hours were subjected to ulcer provocation by pylorus ligature (under diethyl ether anaesthesia) and oral administration of 100 mg/10 ml/kg of acetylsalicylic acid. The substances to be tested are administered orally (10 ml/kg) 1 hour before the pylorus ligature. The wound is closed by means of Michel clamps. 4 hours thereafter, the animals are killed under ether anaesthesia by atlas dislocation, and the stomach is removed. The stomach is opened longitudinally and fixed to a cork tile after the amount of gastric juice secreted (volume) has been determined; the number and size (=diameter) of ulcers present are determined with a stereomicroscope with 10-fold magnification. The product of the degree of severity (according to the following rating scale) and the number of ulcers serves as the individual ulcer index.

| Scale of points: | | |
|---|---|---|
| no ulcers | | 0 |
| ulcer diameter | 0.1–1.4 mm | 1 |
| | 1.5–2.4 mm | 2 |
| | 2.5–3.4 mm | 3 |
| | 3.5–4.4 mm | 4 |
| | 4.5–5.4 mm | 5 |

| Scale of points: | |
|---|---|
| >5.5 mm | 6 |

The reduction in the average ulcer index of each treated group compared with that of the control group (=100%) serves as a measure of the antiulcerogenic effect. The $ED_{50}$ designates the dose which reduces the average ulcer index by 50%.

Determination of toxicity

The toxicity investigations are carried out on female NMRI mice (body weight: 22 to 26 g). The animals (5 animals per dose) receive feed and water ad libitum. Various doses of the substances are administered intravenously (injection time: 1 minute). The observation period is 7 days. The $LD_{50}$ (the dose at which 50% of the animals die) is determined by means of linear regression.

The invention and its advantages are readily understood from the preceding description. Various changes may be made in the synthesis, the intermediates, the pharmacologically-active final products, the dosage forms, the medicament compositions and the mode of administration without departing from the spirit and scope of the invention or sacrificing its material advantages. The hereinbefore described aspects of the subject invention are merely illustrative of preferred embodiments.

What is claimed is:

1. A substituted thienobenzodiazepinone of the formula

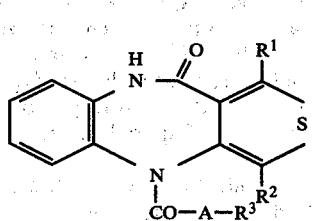

wherein
$R^1$ denotes a hydrogen atom (-H) or alkyl with from 1 to 4 carbon atoms,
$R^2$ represents halo or has one of the meanings of $R^1$,
$R^3$ denotes halo or -N($R^4$)$R^5$,
$R^4$ denotes alkyl with from 1 to 4 carbon atoms or alkenyl with from 3 to 5 carbon atoms,
$R^5$ denotes one of the meanings of $R^4$ or —(CH$_2$-)$_m$—N($R^6$)$R^7$ or N($R^4$)$R^5$ denotes morpholino, pyrrolidino, piperidino, hexahydroazepin-1-yl, piperazin-1-yl which is optionally substituted in the 4-position by methyl, ethyl or benzyl, 2,4-dimethylpiperazin-1-yl or hexahydro-1H-1,4-diazepin-1-yl which is substituted in the 4-position by methyl or ethyl,
$R^6$ denotes alkyl with from 1 to 4 carbon atoms,
$R^7$ denotes alkyl with from 1 to 4 carbon atoms,
A denotes straight-chain or branched alkylene with from 1 to 5 carbon atoms and
m denotes 2 or 3,
or an acid-addition salt thereof.

2. A substituted thienobenzodiazepinone according to claim 1 wherein $R^3$ denotes —N($R^4$)$R^5$, or a acid-addition salt thereof.

3. A thienobenzodiazepinone according to claim 1 wherein
$R^1$ denotes —H or alkyl with from 1 to 4 carbon atoms,
$R^2$ represents halo or has one of the meanings of $R^1$,
$R^3$ denotes —N($R^4$)$R^5$,
$R^4$ denotes alkyl with from 1 to 4 carbon atoms or alkenyl with from 3 to 5 carbon atoms,
$R^5$ has one of the meanings of $R^4$ or represents —(CH$_2$-)$_m$—N($R^6$)$R^7$, or N($R^4$)$R^5$ denotes morpholino, pyrrolidino, piperidino, hexahydroazepin-1-yl, piperazin-1-yl which is optionally substituted in the 4-position by methyl, ethyl or benzyl, 2,4-dimethylpiperazin-1-yl or hexahydro-1H-1,4-diazepin-1-yl which is substituted in the 4-position by methyl or ethyl,
$R^6$ denotes alkyl with from 1 to 4 carbon atoms,
$R^7$ denotes alkyl with from 1 to 4 carbon atoms,
A denotes straight-chain or branched alkylene with from 1 to 5 carbon atoms and
m denotes 2 or 3,
or a pharmacologically-acceptable acid-addition salt thereof.

4. A substituted thienobenzodiazepinone according to claim 3 wherein
$R^1$ denotes a hydrogen atom, methyl or ethyl,
$R^2$ represents chloro or one of the meanings of $R^1$,
$R^3$ denotes —N($R^4$)$R^5$,
$R^4$ denotes alkyl with from 1 to 4 carbon atoms or alkenyl with from 3 or 4 carbon atoms,
$R^5$ has the meaning of $R^4$ or denotes morpholino, pyrrolidino, piperidino, hexahydroazepin-1-yl, piperazin-1-yl which is substituted in the 4-position by methyl, ethyl or benzyl, 2,4-dimethylpiperazin-1-yl or hexahydro-1H-1,4-diazepin-1-yl which is substituted in the 4-position by methyl or ethyl,
$R^6$ denotes methyl or ethyl,
$R^7$ denotes methyl or ethyl,
m denotes 2 or 3 and
A denotes straight-chain or branched alkylene with 1 or 2 carbon atoms,
or an acid-addition salt thereof.

5. A compound according to claim 3 in which $R^1$ denotes —H, methyl or ethyl; $R^2$ represents chloro or has one of the meanings of $R^1$; $R^4$ denotes methyl or ethyl, $R^5$ has the meaning of $R^4$ or represents —(CH$_2$-)$_m$—N($R^6$)$R^7$, or —N($R^4$)$R^5$ denotes pyrrolidino, piperidino or hexahydroazepin-1-yl; each of $R^6$ and $R^7$ denotes methyl or ethyl; m denotes 2; and A denotes methylene; or a pharmacologically-acceptable acid-addition salt thereof.

6. A compound according to claim 3 in which $R^1$ denotes —H, methyl or ethyl; $R^2$ represents chloro or has one of the meanings of $R^1$; $R^4$ and $R^5$, together with the nitrogen atom to which both are bound, denote piperazin-1-yl which is substituted in the 4-position by methyl or ethyl; and A denotes methylene; or a pharmacologically-acceptable acid-addition salt thereof.

7. A compound according to claim 3 in which $R^1$ denotes —H or methyl; $R^2$ denotes —H or methyl; $R^4$ and $R^5$, together with the nitrogen atom to which both are bound, denote piperazin-1-yl which is substituted in the 4-position by methyl; and A denotes methylene; or a pharmacologically-acceptable acid-addition salt thereof.

8. A compound according to claim 3 which is 9,10-dihydro-4-[(4-methylpiperazin-1-yl)acetyl]-4H-thieno[3,4-b][1,5]benzodiazepin-10-one or a pharmacologically-acceptable acid-addition salt thereof.

9. A compound according to claim 3 which is 9,10-dihydro-3-methyl-4[(4-methylpiperazin-1-yl)acetyl]-

4H-thieno[3,4-b][1,5]benzodiazepin-10-one or a pharmacologically-acceptable acid-addition salt thereof.

10. A medicament composition in which a pharmaceutical excipient is combined with a compound according to claim 3, the amount of the latter being from 0.5 to 95 percent by weight of the composition.

11. A medicament composition having a pharmaceutical excipient and a sufficient amount, per unit dose, of a compound according to claim 3 to prevent or reduce the effects of stomach or intestinal disorders.

12. A medicament composition having, per unit dose, a pharmaceutical excipient and from 0.1 to 500 mg of a compound according to claim 3.

13. A method for the prophylaxis or treatment of a stomach or intestinal disorder of the type of acute and chronic ulcus ventriculi and ulcus duodeni, gastritis and hyperacid gastric irritation which comprises administering to a mammal subject to or afflicted with such a disorder an effective amount of a compound according to claim 7.

14. A method for the prophylaxis or treatment of acute and chronic ulcus ventriculi and ulcus duodeni, gastritis and hyperacid gastric irritation which comprises administering to a mammal subject to or afflicted with such a disorder an effective amount of a compound according to claim 3.

* * * * *

UNITED STATES PATENT AND TRADEMARK OFFICE
CERTIFICATE OF CORRECTION

PATENT NO. : 4,381,301

DATED : April 26, 1983

INVENTOR(S) : Georg RAINER

It is certified that error appears in the above-identified patent and that said Letters Patent are hereby corrected as shown below:

Title page, right-hand column, under "OTHER PUBLICATIONS", line 2, correct the spelling of "*Chemotherapy*". Column 3, line 13, "{2-[2'" should read --{2-[(2'--. Column 5, line 46, delete "B". Column 6, line 26, "stomach of" should read --stomach or--;
Column 12, line 17, "$R_3$" should read --$R^3$--.
Column 20, line 27, after "or" insert -- -$N(R^4)R^5$--.

Signed and Sealed this

Seventh Day of February 1984

[SEAL]

Attest:

GERALD J. MOSSINGHOFF

Attesting Officer     Commissioner of Patents and Trademarks